US011129502B1

(12) United States Patent
Jalbert

(10) Patent No.: US 11,129,502 B1
(45) Date of Patent: *Sep. 28, 2021

(54) TOUCHLESS SANITIZING APPARATUS

(71) Applicant: Vincent Paul Jalbert, East Lyme, CT (US)

(72) Inventor: Vincent Paul Jalbert, East Lyme, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/302,945

(22) Filed: May 17, 2021

Related U.S. Application Data

(63) Continuation-in-part of application No. 17/247,457, filed on Dec. 11, 2020, now Pat. No. 11,007,293.

(51) Int. Cl.

| | |
|---|---|
| ***A47K 5/12*** | (2006.01) |
| ***A61L 2/22*** | (2006.01) |
| ***B66B 1/52*** | (2006.01) |
| ***E05F 15/73*** | (2015.01) |

(52) U.S. Cl.
CPC .......... *A47K 5/1217* (2013.01); *A47K 5/1202* (2013.01); *E05F 15/73* (2015.01); *E05F 2015/765* (2015.01)

(58) Field of Classification Search
CPC . A61L 2/22; B66B 1/52; A47K 5/1217; E05F 15/73
See application file for complete search history.

(56) References Cited

FOREIGN PATENT DOCUMENTS

WO WO-2019234064 A2 * 12/2019 ............... A61L 2/10

* cited by examiner

*Primary Examiner* — Kevin Joyner
(74) *Attorney, Agent, or Firm* — Keeley DeAngelo LLP; W Scott Keeley

(57) ABSTRACT

The present disclosure refers to a touchless and motion-sensing hand sanitizing dispenser that also engages a switch. In some embodiments the hand-sanitizing dispenser functions as a door-opening pushbutton for an automatic door system. The embodiment may be used with existing systems or configured for new installations.

8 Claims, 8 Drawing Sheets

TOUCHLESS SANITIZING APPARATUS

The present application is a continuation-in-part of application Ser. No. 17/247,457.

TECHNICAL FIELD

The invention relates in general to liquid dispensers, and more specifically to hand-sanitizing dispensers. The invention further relates to electric switches, optical sensors and optical sensors used to generate signals that are in turn used to activate an external/remote device.

BACKGROUND

Public reaction to COVID-19 has brought about an increase in the application and use of automatic dispensers. Automatic dispensers are common and include soap and hand-sanitizing dispensers. In an example of the state of the art, one places one's hands under a dispensing nozzle and in proximity of a sensor. The activated sensor actuates a pump that dispenses a premeasured amount of liquid, usually soap or hand sanitizer. Common automatic dispensers use sensors to detect the proximity of a hand.

Common sensors include infrared or ultrasound energy sent from and reflected back to the sensor in a regular pattern. A hand in proximity of the sensor bounces back irregularly which triggers the dispensing mechanism.

A photo sensor includes a light source and a light sensor. When the light beam is broken by a user's hands, the dispensing mechanism is activated.

A passive infrared sensor measures infrared energy emitted by a user's body heat. A hand in proximity of a passive infrared sensor causes the infrared energy to fluctuate, triggering a dispensing mechanism.

Touchless devices have become ubiquitous during the time of the COVID-19 pandemic to clean environments and stop the transmission of bacteria found on handles, faucet valves, pump mechanisms and other fomites.

Publicly accessed switches are regularly touched by many people without being cleaned between uses. Automatically sanitizing the hands of everyone in contact with a particular switch is one way to stop the transmission of bacteria. A graphic representation of a button, referred to as a button target, coupled with a proximity sensor that activates a switch when an object comes within proximity, provides a touchless button.

SUMMARY

In accordance with example embodiments of the present disclosure, provided here is an apparatus for combining an automatic hand-sanitizing mechanism with a remote activation function possibly a switch or another signaling method. In one example embodiment a touchless, motion-sensing hand-sanitizing device has a motion sensor that signals an electronic control circuit to engage a switch while dispensing a measure of hand sanitizer. In another example embodiment a touchless, motion-sensing hand-sanitizing device has a motion sensor that signals an electronic control circuit to engage a switch configured to energize an automatic door-opening device, while dispensing a measure of hand sanitizer. Systems and methods are provided so that a switch configured with the present embodiment will continue to function when the dispensing apparatus fails due to a dispensing malfunction or an empty sanitizer reservoir.

One skilled in the art understands that a switch may be engaged to open or close a door, turn lights on or off, call an elevator, or the like. One skilled in the art also understands that material such as hand sanitizer may be dispensed in the form of a liquid or an aerosol like substance. The term fluid is used to describe any liquid or gas. It is understood in the art that public understanding of the use of such devices is common.

Other objects and features will become apparent from the following detailed description considered in conjunction with the accompanying drawings. It is to be understood, however, that the drawings are designed as an illustration and not as a definition of the limits of the invention.

DESCRIPTION

Figure 1:
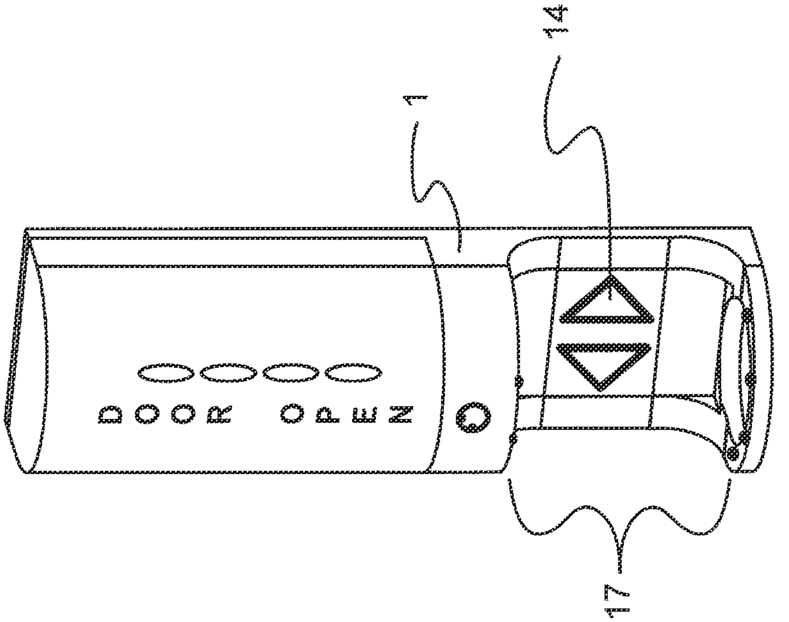
FIG. 1 is a perspective view of the present disclosure.

FIG. 1 is a perspective view of an example embodiment 1. A button target 14 is a door opening. In some embodiments, a raised door-opening button target 14 is located at the back wall of a dispensing bay 17.

Figure 2:
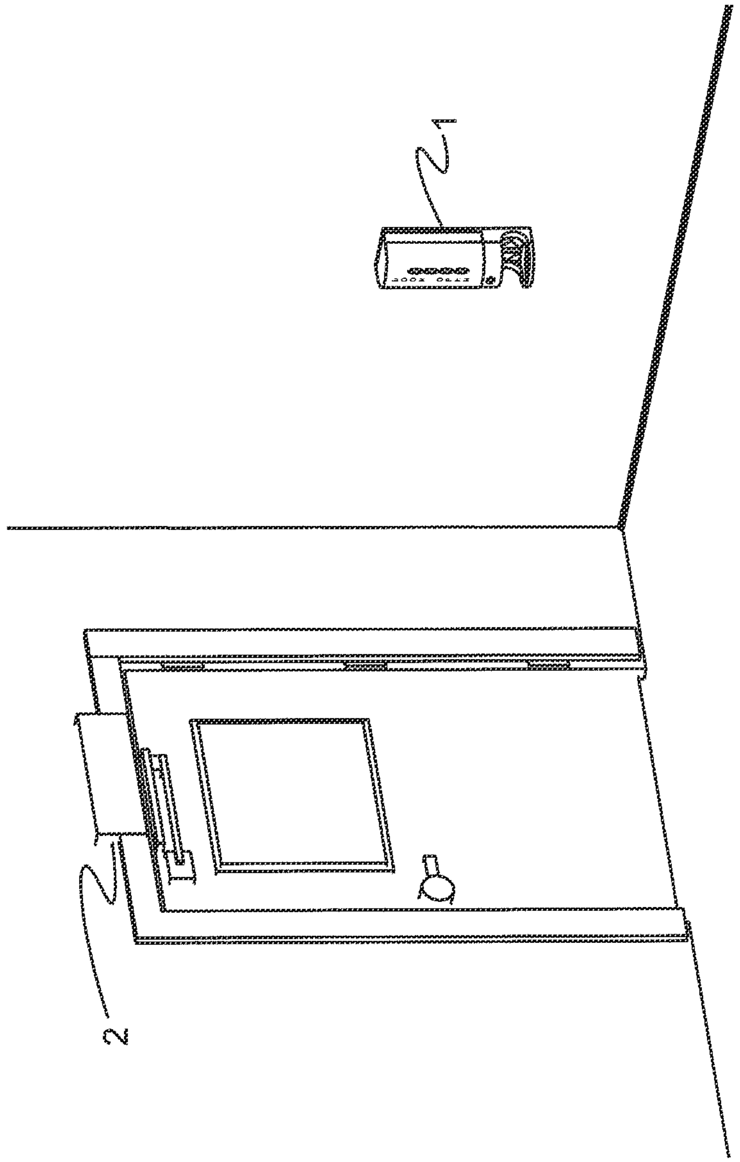
FIG. 2 is a perspective view of an example embodiment installed adjacent to an automatic door.

In FIG. 2, an example embodiment 1 is shown installed in a hall in place of a traditional door-opening push button. A door is automatically operated by a door operator 2.

Figure 3:
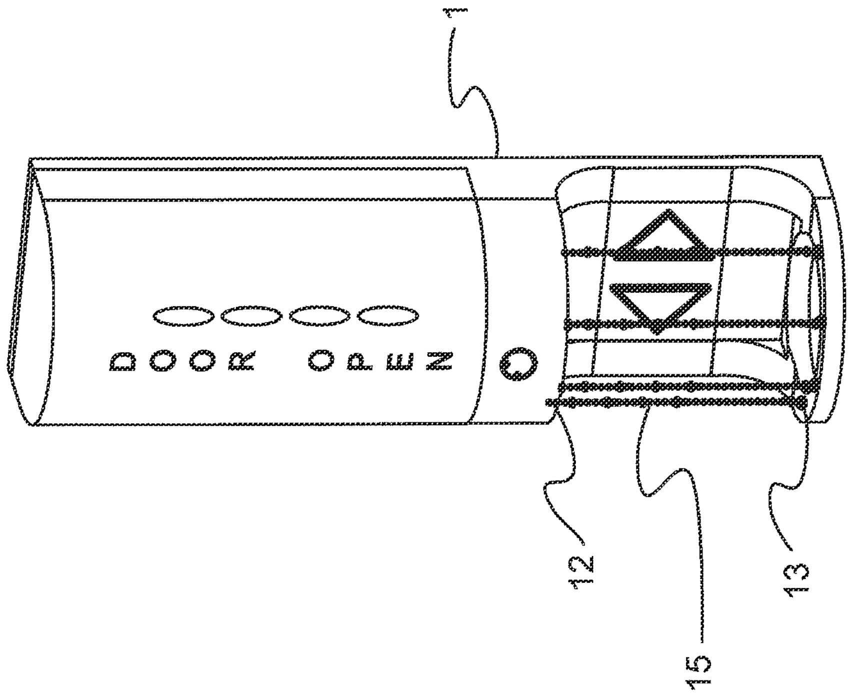
FIG. 3 is a perspective view with a visualization of the infrared detection beams thereof.

In FIG. 3, example embodiment 1, an infrared sensor array detects the motion and position of a human hand or a like-sized object in the dispensing bay 17. LED-focused infrared transmitters and receivers in the semicircle array 13 are arranged within the device in a semicircular array 12 and are more fully described in FIG. 7. A pattern of infrared beams 15 is established between the focused infrared transmitters and the focused infrared receivers (described fully in FIG. 7).

Figure 4:
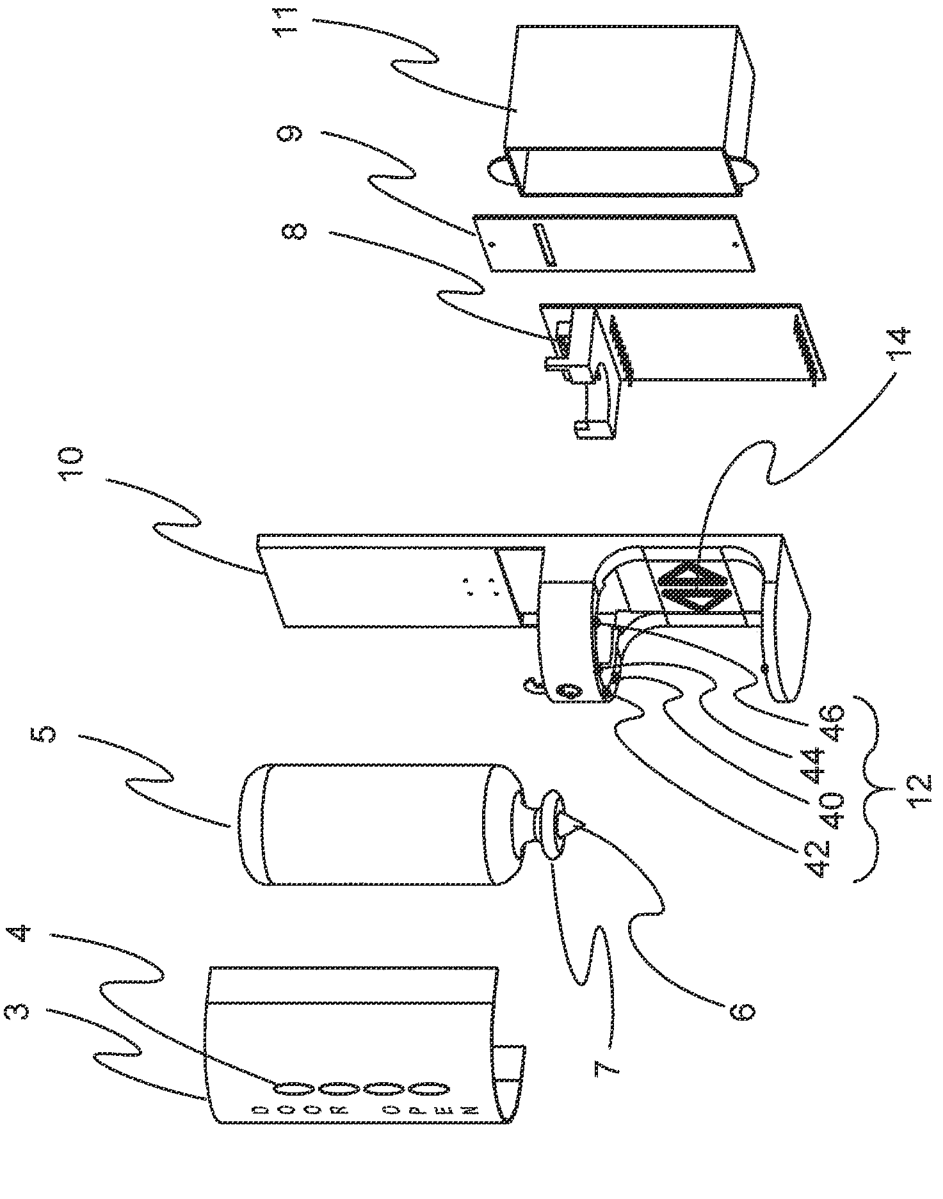
FIG. 4 is an exploded view identifying the major components of the present disclosure.

FIG. 4 shows the major components of example embodiment 1. The device housing 10 is constructed of metal or equivalent and the raised button target 14 is oriented on the back wall of the device. A removable dispenser cover 3 includes cover windows 4 to view the level of dispensing solution. A removable and transparent dispensing reservoir assembly 5 has an integrated release actuator including a connector 22 (FIG. 6), an electric pump 7 (FIG. 4), and a dispensing nozzle 6. As is the case with soap dispensers, this dispensing reservoir assembly 5 must be replaced or refilled routinely. The control circuit assembly 8 is shown in its relative position. A wall box 11 is used for field wiring and is shown for reference; it is not part of the invention. There is a box cover and mounting plate 9.

Figure 5:
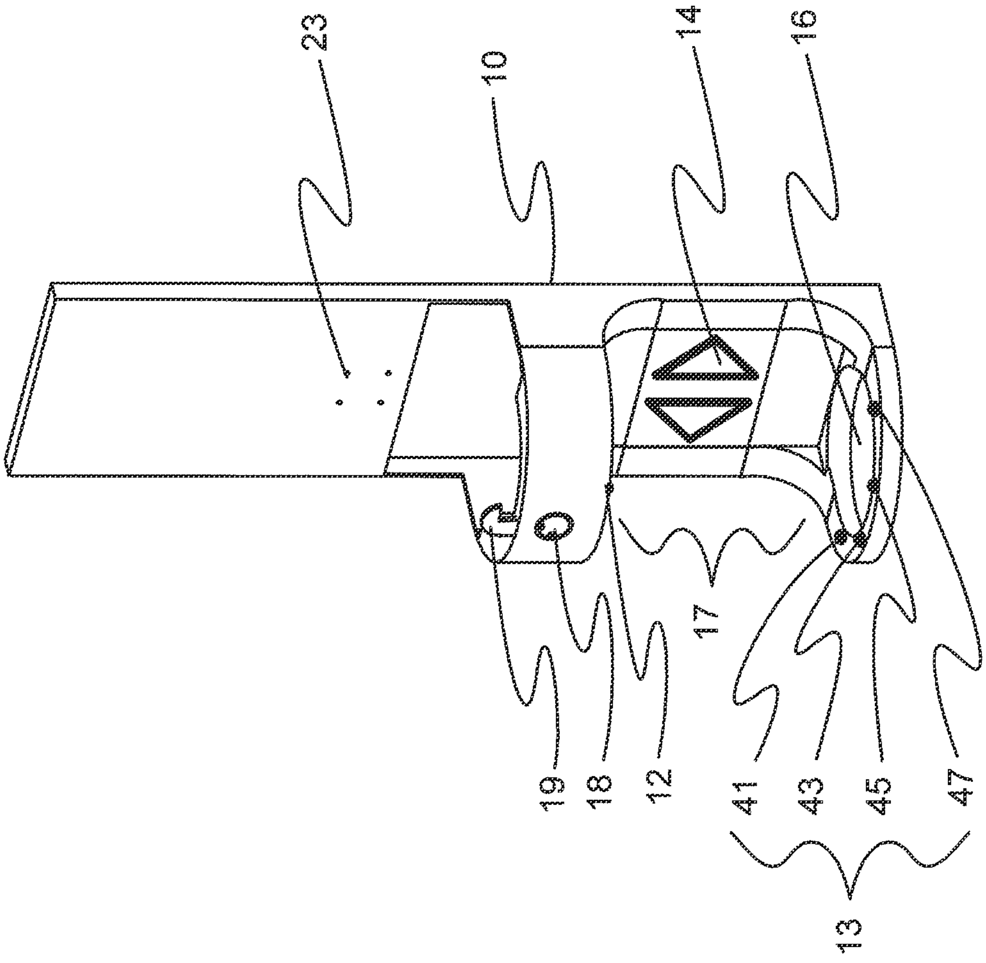
FIG. 5 is a perspective view of housing-related components of the present disclosure.

FIG. 5 shows a device housing 10, the base of which includes a drip pan 16 typical of this type of dispenser system. The dispensing bay 17 includes a raised-button target 14 on the back wall of the device housing 10. The device housing 10 also includes an integrated array of focused infrared receivers 41, 43, 45, and 47 arranged in a semicircle array 13 on the base of the device housing 10. The device housing 10 includes a cover lock 18 and a cover latch 19 to secure the dispenser cover 3 (FIG. 4) in place. The cover lock 18 ensures that only authorized personnel have access to replace or refill the dispensing reservoir assembly 5 (FIG. 4). Mounting holes 23 attach the device housing 10 to the mounting plate 9 (FIG. 4).

Figure 6:
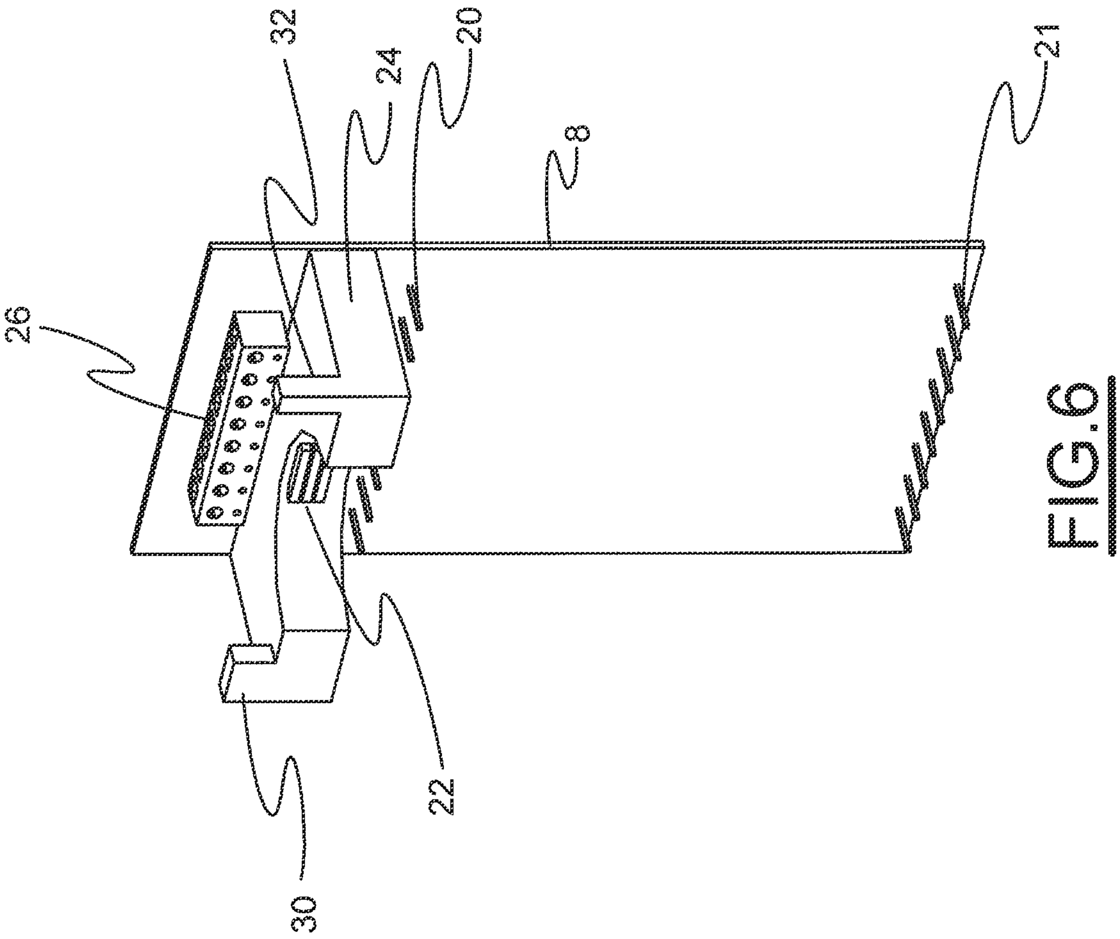
FIG. 6 is a perspective view of an example embodiment of a control circuit of the present disclosure.

FIG. 6 shows a control-circuit assembly 8 of the example embodiment 1. The control circuit assembly includes a microcontroller 29 (FIG. 7) to perform sensing and control functions. The terminal block 26 is for field wiring connections. A control-circuit assembly frame 24 and a dispensing reservoir assembly connector 22 interface with and connect to the dispensing reservoir assembly 5 (FIG. 4).

The control circuit assembly frame 24 also includes an optical cover sensor 32 and a Near Field Communication (NFC) antenna 30. When the dispenser cover 3 (FIG. 4) is removed, the optical cover sensor 32 will force the system into diagnostic and setup mode. An app on a smartphone communicates with the microcontroller 29 (FIG. 7) via an NFC antenna 30 and an NFC Interface 31. The smartphone app enables parameter adjustments. Adjustment parameters include idle time, centered time, accepted beam patterns, dispensing time, activation delay time, and relay-pulse time.

Figure 7:
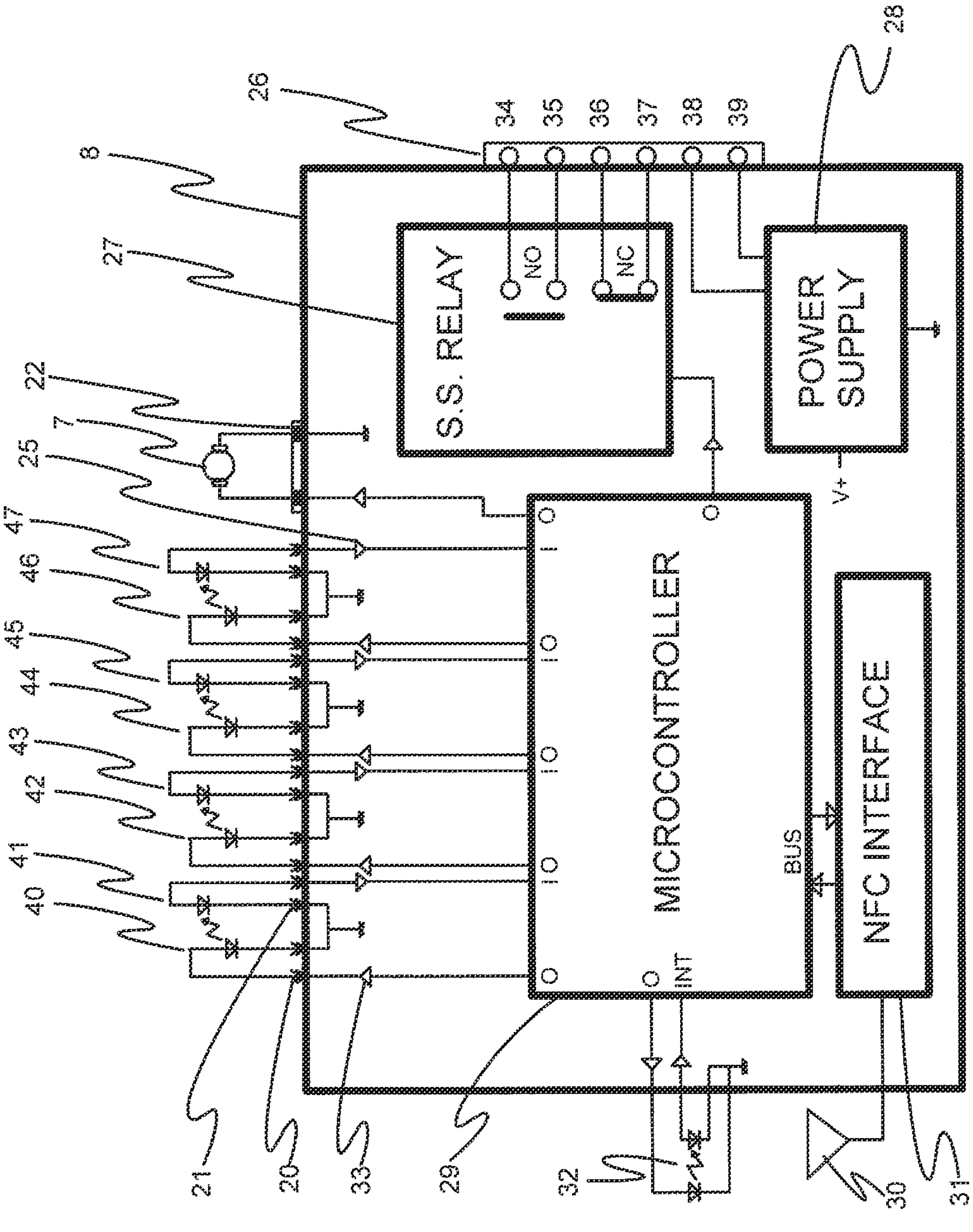
FIG. 7 is an electronic schematic diagram of the present disclosure.

FIG. 7 shows a logical view of the control circuit assembly 8 and the other related components in the form of a systems block diagram. FIG. 7 includes items described in FIG. 6 as well as additional items necessary to complete the features and functions of the embodiment. The control circuit assembly 8 includes a microcontroller 29 which performs all logic and data-processing functions.

The primary function of the control circuit assembly 8 is to detect the presence of a human hand or like-sized object in the dispensing bay 17 (FIG. 5) and respond by dispensing a hand-sanitizing solution and then sending a door-open request to automatic door-opener 2 (FIG. 2).

A number of microcontroller buffer driver circuits 33 and receiver circuits 25 are required to interface with device components. The LED infrared semicircle array 12 is comprised of four infrared LEDS 40, 42, 44, and 46 that are connected to the control circuit assembly via connector 20. Corresponding infrared receivers 41, 43, 45, and 47 make up the receiver semicircle array 13 (FIG. 3) and are connected to the control-circuit assembly 8 via connector 21. The microcontroller connects to the dispensing electric pump 7 (FIG. 4) via the interface connector 22. A solid-state relay 27 is controlled by microcontroller 29 and is used to activate the automatic door opener by simulating a mechanical push button. All external connections with the control-circuit assembly are made via the field wiring terminal block 26. Terminals 34 and 35 on the field wiring terminal block 26 provide signals for a normally open push-button interface. Terminals 36 and 37 on the field wiring terminal block 26 provide signals for a normally closed push button interface. Terminals 38 and 39 on the field wiring terminal block 26 provide power input connections for the onboard power supply 28. The onboard power supply converts and regulates the voltages to operate the control circuit assembly 8.

When the cover 3 (FIG. 4) is removed the optical cover sensor 32 (FIG. 6) forces the microcontroller into setup and diagnostic mode. In the setup and diagnostic mode, a Near Field Communication (NFC) Interface 31 and an NFC antenna 30 manage all the device's wireless communication in the setup and diagnostic mode of operation between the microcontroller 29 and a smartphone app.

The device housing 10 (FIG. 5) includes an integrated array of LED focused-infrared beam transmitters 40, 42, 44, and 46 arranged in a semicircle array 12 on the top edge of the device housing 10. This array has an electrical connection to the control circuit via a connector 20. An array of focused-infrared receivers 41, 43, 45, and 47 is also arranged in a semicircle array 13. A pattern of infrared beams 15 is established between the focused infrared transmitters 40, 42, 44, and 46 and the focused infrared receivers 41, 43, 45, and 47. When a human hand or like-sized object enters and moves through the dispensing bay 17 (FIG. 5), the infrared beams are interrupted, allowing the hand or like-sized object to be tracked by a control circuit assembly 8 (FIG. 4) in the dispensing bay 17. One skilled in the art understands that although an infrared sensor is shown in the example embodiment, other sensors may be used to measure the proximity of a human hand to signal the initiation of a sequence for dispensing hand sanitizer and engaging a switch to open a door. One skilled in the art further understands that although a door opening button is shown in the example, the embodiment may be configured to engage any button or switch.

Figure 8:
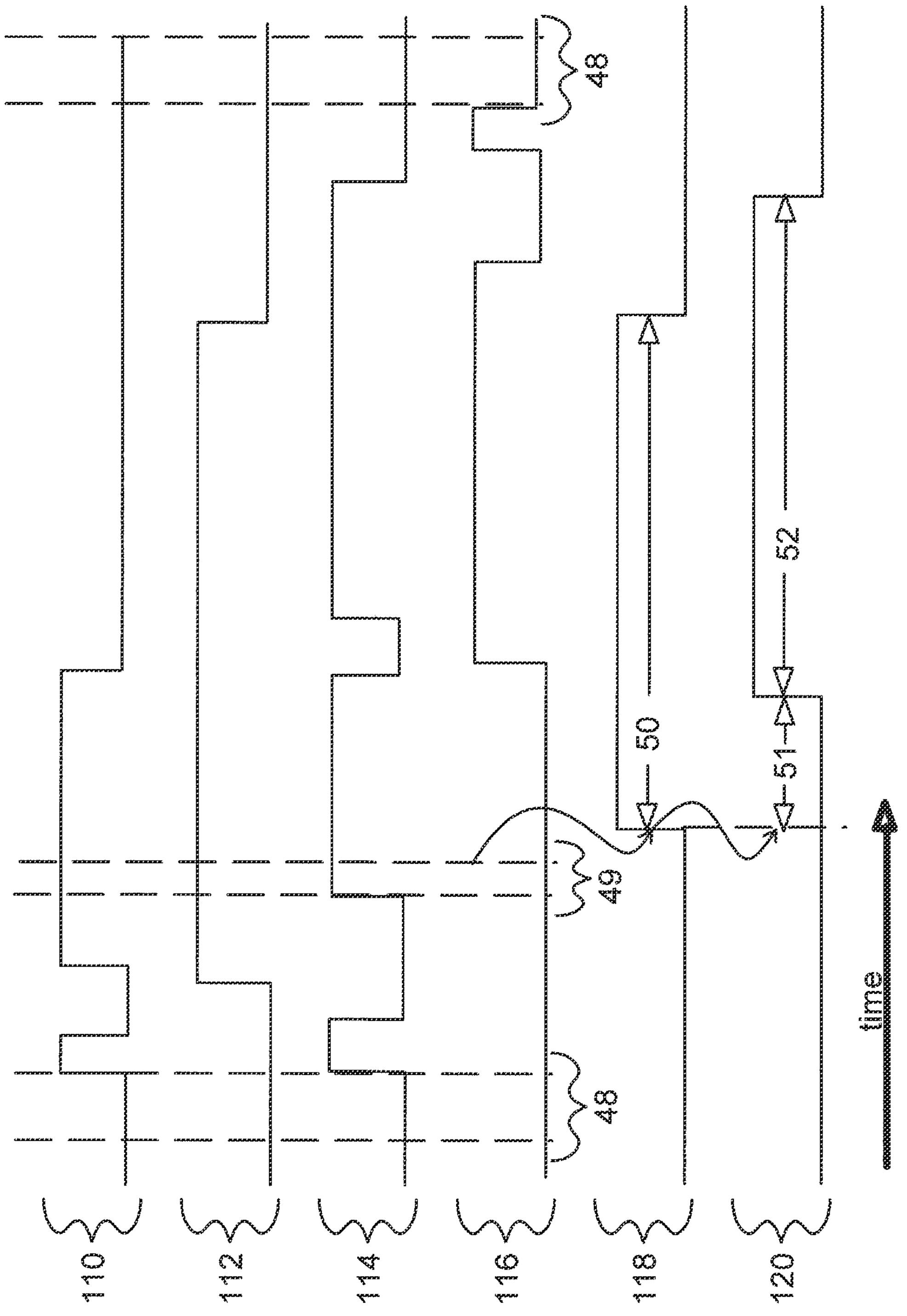
FIG. 8 is an electronic schematic diagram of the present disclosure illustrating a timing sequence.

FIG. 8 illustrates a timing diagram for one cycle of the example embodiment. One cycle of the invention 1 includes the following actions by the microcontroller 29 (FIG. 7):

Detection of a human hand or similar sized object in the dispensing bay 17.

Dispensing of a dose of hand-sanitizing solution into a hand in the dispensing bay 17.

A simulated button-push to activate a connected automatic door operating system 2, to open a door.

Line 110 represents the signal received by the infrared receiver 41, wherein a clear beam is represented by a low state and a blocked beam is represented by a high state.

Line 112 represents the signal received by the infrared receiver 43, wherein a clear beam is represented by a low state and a blocked beam is represented by a high state.

Line 114 represents the signal received by the infrared receiver 45, wherein a clear beam is represented by a low state and a blocked beam is represented by a high state.

Line 116 represents the signal received by the infrared receiver 47, wherein a clear beam is represented by a low state and a blocked beam is represented by a high state.

Line 118 is the microcontroller generated dispensing signal for the release of the hand sanitizing solution via the electric pump 7.

Line 120 is the microcontroller generated door activation signal sent to the door opener 2 via the solid-state relay 27.

Before a cycle can begin there is a prerequisite minimum idle period 48 that must be met to confirm that the dispensing bay 17 (FIG. 5) is empty. The cycle start requires that a specified set of infrared beams must be interrupted and remain in a stable state for a minimum start-time duration 49. The prerequisite set of interrupted beams is a programmable parameter and can include more than one set of interrupted beams. Once the conditions for a cycle start are met, the dispensing pulse is generated by the microcontroller 29 (FIG. 7). The duration of the dispensing pulse 50 is programmable. The start of the dispensing pulse triggers an activation delay 51 to ensure customers have time to receive the dose of hand-sanitizing solution before the automatic door starts to open. At the end of the activation delay 51, a door-activation signal is generated by the microcontroller for a programmable duration 52. The cycle will end when the prerequisite minimum idle-time period 48 is present again.

The example embodiments have been described herein should not be construed as limiting.

The invention claimed is:

1. An apparatus for both dispensing hand sanitizer and engaging a switch comprising:

a housing; and a reservoir in said housing, configured to contain sanitizing fluid; and an actuated valve fluidly engaged with said reservoir configured to dispense sanitizing fluid; and at least one sensor configured to sense object motion and to signal the activation of said actuated valve; and a button target engaged with said housing proximal to said at least one sensor; and a conventional door-opening mechanism; wherein an object approaches said button target proximal to said at least one sensor, signals the activation of said actuated valve, dispenses hand sanitizer and further signals the engagement of said switch, and engagement of said switch activates said conventional door-opening mechanism.

2. The apparatus of claim 1 further comprising:

at least one dispensing bay fixedly engaged with said housing proximal to said at least one sensor; wherein the dispensing bay shows a user where to place an object to be in proper proximity of said button target to signal engagement of said switch.

3. The apparatus of claim 1 further comprising:

an electronic delay between actuation of said actuated valve and signaling engagement of said switch; wherein a user must take time to receive hand sanitizer prior to the engagement of said switch.

4. The apparatus of claim 1 further comprising:

a control circuit configured to receive a signal from said at least one sensor and activate said actuated valve, and to receive a signal from said at least one sensor, in turn to send a signal to activate a conventional door-opening mechanism.

5. The apparatus of claim 3 further comprising:

a semicircular array of infrared LEDs and corresponding semicircular array of infrared receivers, electrically coupled with said control circuit; and said control circuit electrically coupled with an electric pump that is fluidly coupled with said reservoir and further coupled with said actuated valve; and a solid state relay electrically coupled with said control circuit and further electrically coupled with a door opener; wherein breaking the light transmitted between said semicircular array of LEDs and said semicircular array of infrared receivers signals said control circuit to engage said electric pump and to engage said solid state relay to engage said door opener.

6. The apparatus of claim 1 wherein said at least one sensor is a combination ultrasound transmitter and ultrasound receiver.

7. An apparatus for both dispensing hand sanitizer and engaging a switch comprising:

a housing; and a reservoir in said housing, configured to contain sanitizing fluid; and at least one dispensing bay within said housing; and an actuated valve fluidly engaged with said reservoir, configured to dispense sanitizing fluid; and a control circuit electrically coupled with at least one sensor and said actuated valve; and an electric pump in fluid communication between said reservoir and said actuated valve;

and electrically coupled with said control circuit: and said at least one sensor configured to sense object motion in the dispensing bay and to send a signal to said control circuit to activate said actuated valve and to signal said control circuit to engage said switch; wherein said control circuit is configured to receive a signal from said at least one sensor to activate said electric pump and said actuated valve; in turn to send a signal to activate a conventional door-opening mechanism, and to dispense said hand sanitizer.

8. A method for using the apparatus of claim 5 comprising:

detecting the presence of at least a portion of a human hand; and dispensing an amount of hand-sanitizing fluid onto said at least a portion of a human hand; and simulating a signaling method to activate a connected, conventional automatic door-opening apparatus.

* * * * *